(12) United States Patent
Glenn et al.

(10) Patent No.: US 7,785,576 B2
(45) Date of Patent: Aug. 31, 2010

(54) DURABLE FIBER TREATMENT COMPOSITION

(75) Inventors: Robert Wayne Glenn, Virginia Water (GB); Simon Paul Godfrey, Middlesex (GB); Anthony McMeekin, Bagshot (GB); Coralie Claude Monique Boumard, Egham (GB); Neil Charles Dring, Medmanham (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/267,096

(22) Filed: Nov. 7, 2008

(65) Prior Publication Data

US 2009/0068135 A1 Mar. 12, 2009

Related U.S. Application Data

(63) Continuation of application No. 10/409,313, filed on Apr. 8, 2003, now abandoned.

(30) Foreign Application Priority Data

Apr. 25, 2002 (GB) .................................. 0209485.2

(51) Int. Cl.
*A61Q 5/00* (2006.01)
*A61Q 5/08* (2006.01)
*A61Q 5/10* (2006.01)
*A61Q 5/12* (2006.01)

(52) U.S. Cl. .................................. 424/70.12; 424/70.6
(58) Field of Classification Search .................. None
See application file for complete search history.

(56) References Cited

U.S. PATENT DOCUMENTS

| | | | |
|---|---|---|---|
| 4,359,545 | A | 11/1982 | Ona |
| 4,409,267 | A | 10/1983 | Ichinohe |
| 4,459,382 | A | 7/1984 | Ona |
| 4,579,131 | A * | 4/1986 | Syed .................. 132/202 |
| 5,710,113 | A | 1/1998 | Wells |
| 6,136,304 | A | 10/2000 | Pyles |
| 6,180,576 | B1 * | 1/2001 | Melby et al. ............ 510/121 |
| 6,255,429 | B1 | 7/2001 | Griffin |
| 6,423,306 | B2 | 7/2002 | Caes et al. |
| 6,984,390 | B2 | 1/2006 | Sakuta |
| 6,986,886 | B2 | 1/2006 | Hammond et al. |
| 7,001,971 | B2 | 2/2006 | Nakanishi |
| 2001/0043912 | A1 | 11/2001 | Michael |

FOREIGN PATENT DOCUMENTS

| | | |
|---|---|---|
| EP | 0275707 A2 | 7/1988 |
| EP | 1081272 A1 | 3/2001 |
| EP | 1175893 A2 | 1/2002 |
| FR | 2780643 A1 | 1/2000 |
| JP | 63-313713 A | 6/1987 |
| JP | 63-051315 A | 3/1988 |
| JP | 1993043696 A | 2/1993 |
| JP | 1998316542 A | 12/1998 |
| JP | 1998330223 A | 12/1998 |
| JP | 2003146832 A | 5/2003 |
| WO | WO-92/10161 A1 | 6/1992 |
| WO | WO-97/32917 A1 | 9/1997 |
| WO | WO-99/29286 A1 | 6/1999 |
| WO | WO-99/49836 A1 | 10/1999 |
| WO | WO-01/25380 A1 | 4/2001 |
| WO | WO-01/15658 A1 | 8/2001 |
| WO | WO-01/91706 A1 | 12/2001 |
| WO | WO 02/22084 * | 3/2002 |
| WO | WO-02/22084 A2 | 3/2002 |

OTHER PUBLICATIONS

Czech, A.M., "Modified Silicone Softeners for Fluorocarbon Soil Release Treatments", *Book of Papers-International Conference and Exhibition*, XP001164014, pp. 230-238, American Association of Textile Chemists and Colorists, Tarrytown, NY.

Schlossmann, M., "The Chemistry and manufacture of cosmetics", vol. 2-formulating, $3^{rd}$ edition, 2000, Allured Publishing Corp., USA, XP002250035, formula 13, p. 386.

* cited by examiner

*Primary Examiner*—Jyothsna A Venkat
(74) *Attorney, Agent, or Firm*—Melissa G. Krasovec; Laura R. Grunzinger

(57) ABSTRACT

A fiber treatment composition is presented comprising organomodified silicones having defined physico-chemical properties and a additive which allows the organomodified silicone to be retained on the hair over longer periods of time than traditionally has been the case. The present composition finds particular application on hair that has been damaged through chemical treatments, such as occurs during permanent dyeing, bleaching and permanent waving.

10 Claims, No Drawings

DURABLE FIBER TREATMENT COMPOSITION

CROSS REFERENCE TO RELATED APPLICATION

This application is a continuation of application Ser. No. 10/409,313, filed Apr. 8, 2003now abandoned.

FIELD OF THE INVENTION

The present invention relates to topical compositions for treating natural and synthetic fibrous substrates. The topical compositions comprise mixtures of functionalized silicones having defined physico-chemical properties with a durability additive. The durability additive is capable of modifying the functionalized silicones to render them more durable on polar fibrous substrates than previously known silicone based conditioners, especially where the substrate is hair that has been previously damaged through chemical treatments, such as occurs during permanent dyeing, bleaching and permanent waving.

BACKGROUND OF THE INVENTION

Oxidative dyeing, otherwise known as permanent colouring leads to irreversible physico-chemical changes to the hair. Typically, during this process, two components are mixed together prior to application to the hair. These components usually comprise an oxidising agent, such as hydrogen peroxide, and a dyeing material, such as oxidative dye precursors and couplers (buffered at a high pH, typically around 10). After contacting with the hair, the mixture is left for a period of time suitable to allow the required colour transformation to occur, after which the hair becomes more hydrophilic versus non-coloured hair due to irreversible chemical changes. While not wishing to be bound by theory, this change in hair hydrophilicity appears to be due, among other things, to the oxidation of the keratin-keratin cysteine amino acids within the hair creating more hydrophilic cysteic acid amino acid residues and the hydrolysis of the hair's natural hydrophobic, protective layer denoted as the F-Layer, a covalently attached lipid to the outer epicuticular envelope, 18-methyleicosanoic acid. This colouring process is usually repeated regularly by consumers in order to maintain their desired hair colour and colour intensity and also to ensure that new hair growth has the same colour as the older hair. As a consequence the hair changes polarity from a relatively hydrophobic surface near the scalp where it could be experiencing its first colour, to a progressively more polar substrate at the hair tips, which may have been subjected to multiple colouring treatments. A discussion of oxidation dyeing of hair can be found in "The Science of Hair Care" by Charles Zviak, Marcel Dekker, New York, 1986. These irreversible physicochemical changes can manifest themselves as increased roughness, brittleness and dryness leading to less manageable hair.

After the colouring process human hair becomes soiled due to its contact with the surrounding environment and from the sebum secreted by the scalp. This soiling of the hair causes it to have a dirty feel and unattractive appearance and necessitates shampooing with frequent regularity. Shampooing cleans the hair by removing excess soil and sebum, but can leave the hair in a wet, tangled, and generally unmanageable state. Once the hair dries, it is often left in a dry, rough, lustreless, or frizzy condition due to the removal of the hair's natural oils and other natural or deposited conditioning and moisturizing components. Hair can also be left with increased levels of static upon drying which can interfere with combing and result in a condition commonly referred to as "fly-away-hair". These conditions tend to be exaggerated on hair which has been previously oxidatively coloured.

It is known to use hair conditioners to alleviate the above problems. More specifically, it is known to add conditioning materials to colorant products or to supply them separately as part of colorant kits. It is also known to use conditioners in the shampooing process. These approaches range from post-shampoo application of hair conditioners such as leave-on or rinse-off products, to hair conditioning shampoos which attempt to both cleanse and condition the hair from a single product. Hair conditioners are typically applied in a separate step following shampooing. The hair conditioners are either rinsed-off or left-on, depending upon the type of product used. Polydimethylsiloxanes (PDMS) are often employed as conditioning materials to improve hair feel. However, it is known that, in the case of more hydrophilic hair obtained after oxidative coloring, PDMS deposition is greatly reduced, and cannot provide the same benefit in hair condition as for non-oxidatively colored hair. Moreover, PDMS based conditioners are not retained on the hair for a sufficient period of time for the benefit to be durable.

The use of more polar silicones, such as amino-functionalized silicones, and even more hydrophilic quat-functionalized silicones is known—reference is made to EP 0 275 707 and WO 99/49836 on the one hand and U.S. Pat. No. 6,136, 304 on the other. However, whereas these exhibit improved deposition onto the more polar damaged hair, their durability on such substrates is poor—the increased polarity renders these silicones more susceptible to removal via washing (thereby reducing durability). Without wishing to be bound by theory, this is believed to result from such silicones having increased aqueous affinity versus the less polar silicones making them more apt to being washed away during shampooing.

The addition of organomodified resins to non-polar polydimethylsiloxanes is known. In WO 92/10161, PDMS-based silicone conditioners are modified by addition of a resin, in that case to improve silicone deposition onto undamaged hair. However, this does not address the issue of durability onto chemically damaged hair: polydimethylsiloxanes are too non-polar for sufficient deposition onto the hydrophilic, chemically damaged hair for even an initial conditioning benefit to be achieved, let alone a durable benefit.

Organomodified siloxane resins have also been added to the very hydrophilic silicone copolyols. US 2001/0043912 is concerned with tackling the problem of "frizzy" hair and proposes to modify dimethicone copolyols by addition of a silicone resin to achieve this aim. This document is not concerned with improving conditioner durability. Moreover, the compositions proposed would not achieve that aim either, since even the resin-modified dimethicone copolyols are far too hydrophilic (100 on the Hydrophilicity Index, detailed below), so would be washed off during any washing step immediately subsequent to application.

With the above discussion in mind, the invention will ideally provide a hair treatment composition comprising a conditioning agent that is durable, i.e. does not wash off so rapidly that the conditioning benefit is lost to the consumer, especially on chemically damaged hair, such as occurs during permanent dyeing, bleaching and permanent waving.

SUMMARY OF THE INVENTION

According to a first aspect of the invention, a fiber treatment composition is presented, which comprises a mixture of (a) a functionalized silicone polymer having an interfacial tension (IFT) of less than or equal to 15 mN/m (15 dyne/cm) and a hydrophilicity index (HI) of less than 100; and
(b) a durability additive which is miscible with the functionalized silicone wherein the mixture has a $(\tan \delta)^{-1}$ greater than zero, and:

$$\tan \delta = G''/G'$$

G' is the storage modulus

G" is the loss modulus

Tan δ describes the ratio of energy lost to energy stored, where Tan $\delta = G''/G'$, G" is the loss modulus and G' is the storage modulus. G" and G' are established by means of the dynamic rheological properties, which, in turn, are measured by an oscillation sweep on a rheometer, as described hereinbelow. More information on the measurement of dynamic rheological properties can be found in "Rheological Properties of Cosmetics and Toiletries" by Dennis Laba, Cosmetic Science and Technology Series, Volume 13, Marcel Dekker, Inc., ISBN 0-8247-9090-1.

For the avoidance of doubt, $(\tan \delta)^{-1}$ is directly equivalent to 1/(Tan δ).

The functionalized silicone polymers according to the invention are capable of depositing durably on hair in all states of damage.

As used herein, the term "fiber" includes strands of natural or synthetic materials. Non-limiting examples of natural materials are amino acid based materials, including protinaceous materials such as wool, human hair, including velus hair, and animal fur; cotton; cellulose and silk. Non-limiting examples of synthetic materials are polyester, nylon and rayon.

As used herein, the term "functionalized silicone" includes polydimethylsiloxanes (PDMS) in which at least one methyl group has been replaced by a different group, which is preferably not hydrogen; the term "functionalized silicone" expressly includes the organomodified silicones, as defined hereinbelow. The term "functional silicone" is synonymous with the term "functionalized silicone".

The terms "interfacial tension" and "hydrophilicity index" are to be understood as defined hereinbelow.

As used herein, the term "durability additive" includes materials which improve the durability of the functionalized silicone, as measured by the Silicone Durability Index Value, as defined hereinbelow. In other words, a durability additive is a material which, when mixed with a functionalized silicone, gives a mixture which is more durable than the functionalized silicone alone.

As used herein, a material Y is "miscible" in a material Z if Y and Z may be mixed to generate a homogenous mixture that does not phase separate at standard conditions of temperature and pressure within 3 weeks following termination of mixing.

The term HLB value is known to the skilled person working in this technical area—see for example Römpp Chemie Lexikon, Thieme Varlag, Stuttgart, 9$^{th}$ Edition, 1995 under "HLB-Wert".

DETAILED DESCRIPTION OF THE INVENTION

All cited references are incorporated herein by reference in their entireties.

All percentages given herein are by weight of total composition unless specifically stated otherwise. All ratios given herein are weight ratios unless specifically stated otherwise.

All molecular weights given herein are weight average molecular weights, unless stated otherwise.

Except where specific examples of actual measured values are presented, numerical values referred to herein should be considered to be qualified by the word "about".

In examining how to solve the above technical problems, the present inventors moved away from focusing exclusively on molecular properties and started also to consider what effect altering physical properties of silicones might have. That is because we observed that silicone droplets tend to interact with strands of hair predominantly as fluids and not as individual molecules. A number of parameters were investigated and matched against the objectives. Functionalized silicones tend to exhibit high dynamic mobility, a low melting point (on the order of −40° C.), a low glass transition temperature (on the order of −100° C.), and correspondingly fit the Newtonian fluid-model well. Without wishing to be bound by theory, this is probably due to their reduced steric interactions versus carbon-based chains (absence of side groups on O and relatively long Si—O & Si—C bond lengths) leading to a resulting 'open' structure, which is responsible for a relatively (to alkanes) low barrier to rotation about the Si—O bond. Being Newtonian fluids, functionalised silicones deform irreversibly, meaning that the fluid does not have a tendency to recover to its original position when an external force is removed and therefore the energy imparted by the external force is fully lost and not stored.

Surprisingly, the present inventors have found that by transforming polar functionalized silicone fluids within a defined hydrophilicity range into moderately viscoelastic fluids with a defined viscoelasticity range, these functionalized silicones can be rendered more durable in relation to chemically damaged hair, while still maintaining the desirable "feel" characteristics of the original functionalized silicones.

Hydrophilicity has traditionally been measured by means of interfacial tension (IFT) which is conventionally established using a pendant drop-type method, as defined hereinbelow. The present inventors also used such a method as far as they were able. During the course of our investigations it became apparent, however, that the accuracy of the pendant drop method drops off significantly for functionalized silicones having interfacial tensions of less than 1 mN/m (1 dyne/cm). This is because the difference in surface energy is so low that the "drop" becomes hard to distinguish from the surrounding medium. Extremely hydrophilic silicones such as Wetsoft CTW, for example, from Wacker Silicones, is so hydrophilic that an IFT measurement using the pendant drop method is extremely difficult to perform. Unfortunately, the hydrophility region we are interested in includes the region of IFT less than 1 mN/m. As a result, the present inventors were forced to adopt an alternative method for this region—the so-called hydrophilicity index (HI) as also defined hereinbelow.

The functionalized silicone fluids of the present invention have an IFT of less than or equal to 15 mN/m and an HI of less than 100, preferably an IFT of less than 12 mN/m and an HI of less than or equal to 99.5, more preferably an IFT of less than 8 mN/m and an HI of less than or equal to 98, more preferably still an IFT of less than 1 mN/m and an HI of less than 99.5, yet more preferably an HI in the range from 87 to 98.

For the sake of completeness, an IFT of 1 mN/m (1 dyne/cm) corresponds to an HI of approximately 85. For ease of comprehension, the lower the IFT value, the higher the corresponding HI value and vice versa.

According to the invention, $(\tan \delta)^{-1}$ is greater than zero, preferably from 0.001 to less than or equal to 0.1. Above this upper limit, the tactile feel performance is reduced, with the mixture of functionalized silicone/additive becoming sticky and tacky to the touch, reducing acceptance by consumers. More preferably, $(\tan \delta)^{-1}$ is from 0.01 to less than or equal to 0.075.

For reference, the following table, Table 1, comprises (Tan $\delta)^{-1}$ values of some commercially available polar functional silicone materials. By mixing such silicones with a durability additive, the value of $(Tan \delta)^{-1}$ can be made greater than zero, thereby improving the durability performance, as demonstrated in Table 2 (see below):

| Commercial Fluid | Supplier | $(\tan \delta)^{-1}$ |
|---|---|---|
| XS69-B5476 | GE Bayer | −0.04 |
| KF861 | Shin Etsu | −0.02 |
| X22-3701E | Shin Etsu | −0.27 |
| Abilsoft AF100 | Goldschmidt | −0.15 |
| Silwet L8500 | OSi Silicones | −0.68 |
| Wetsoft CTW | Wacker | −0.09 |
| DC2-8211 | Dow Corning | −0.19 |
| DC8566 | Dow Corning | −0.10 |
| Rhodorsil 21637 | Rhodia | −0.51 | wherein instrumental negative $(Tan \delta)^{-1}$ values indicate a $(Tan \delta)^{-1}$ value of zero According to an embodiment of the invention, the ratio of the weight of functionalized silicone to durability additive is in the range from 5:1 to 1000:1, preferably from 10:1 to 1000:1 and more preferably from about 20:1 to about 1000:1.

Fiber treatment compositions according to an embodiment of the invention may comprise from 0.1 to 20%, preferably from 0.50 to 15%, more preferably from 0.50 to 10% and more preferably still from 0.5 to 7.5% by weight of the mixture of functionalized silicone fluid and durability additive.

Functionalized silicones which may be incorporated into compositions according to the invention include organomodified silicones of the pendant or graft type wherein polar functional substituents are incorporated within or onto monovalent organic groups, $A^1$, $A^2$, $A^3$ and $A^4$ used hereinafter, as follows:

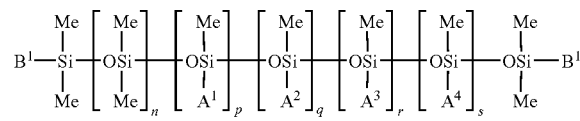

Also included are the organomodified silicones of the block copolymer type wherein these polar functional substituents are incorporated within or onto bivalent organic groups, $A^1$, $A^2$, $A^3$ and $A^4$ used hereinafter.

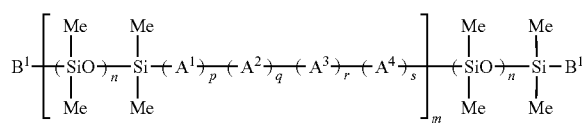

where Me is methyl, m is greater than or equal to 1, n is about 50 to 2000, p is about 0 to 50, q is about 0 to 50, r is about 0 to 50, s is about 0 to 50, wherein p+q+r+s is greater than or equal to 1, $B^1$ is H, OH, an alkyl or an alkoxy group.

The above functionalized silicones of the pendant or block copolymer type can also incorporate silicone branching groups including $MeSiO_{3/2}$, known as silsesquioxane or T groups, and $SiO_{4/2}$, known as Q groups by those skilled in the art.

Organic groups $A^1$, $A^2$, $A^3$ and $A^4$ may be straight, branched or mono- or polycyclic aliphatic, mono or polyunsaturated alkyl, aryl, heteroalkyl, heteroaliphatic or heteroolefinic moiety comprising 3 to 150 carbon atoms together with 0-50 heteroatoms, especially O, N, S, P and can incorporate one or more polar substituents selected from electron withdrawing, electron neutral, or electron donating groups with Hammett sigma para values between −1.0 and +1.5 which can be non-ionic, zwitterionic, cationic or anionic comprising, for example, groups $\alpha^1$, $\alpha^2$, $\alpha^3$, and $\alpha^4$ as defined below; S-linked groups including $S\alpha^1$, SCN, $SO_2\alpha^1$, $SO_3\alpha^1$, $SS\alpha^1$, $SO\alpha^1$, $SO_2N\alpha^1\alpha^2$, $SN\alpha^1\alpha^2$, $S(N\alpha^1)\alpha^2$, $S(O)(N\alpha^1)\alpha^2$, $S\alpha^1(N\alpha^2)$, $SON\alpha^1\alpha^2$; O-linked groups including $O\alpha^1$, $OO\alpha^1$, OCN, $ON\alpha^1\alpha^2$; N-linked groups including $N\alpha^1\alpha^2$, $N\alpha^1\alpha^2\alpha^3+$, NC, $N\alpha^1O\alpha^2$, $N\alpha^1S\alpha^2$, NCO, NCS, $NO_2$, $N=N\alpha^1$, $N=NO\alpha^1$, $N\alpha^1CN$, $N=C-N\alpha^1$, $N\alpha^1N\alpha^2\alpha^3$, $N\alpha^1N\alpha^2N\alpha^3\alpha^4$, $N\alpha^1N=N\alpha^2$; other miscellaneous groups including COX, $CON_3$, $CON\alpha^1\alpha^2$, $CON\alpha^1CO\alpha^2$, $C(=N\alpha^1)N\alpha^1\alpha^2$, CHO, CHS, CN, NC, and X.

$\alpha^1$, $\alpha^2$, $\alpha^3$, and $\alpha^4$ may be straight, branched or mono or polycyclic aliphatic, mono or polyunsaturated alkyl, aryl, heteroalkyl, heteroaliphatic or heteroolefinic moiety comprising 3 to 150 carbon atoms together with 0-50 heteroatoms, especially 0, N, S, P.

X is F, Cl, Br, or I.

H is hydrogen, O is oxygen, N is nitrogen, C is carbon, S is sulfur, Cl is chlorine, Br is bromine, I is iodine, F is fluorine.

Hammett sigma para values are discussed in Römpp Chemie Lexikon, Georg Thieme Verlag, Stuttgart, N.Y., $9^{th}$ Edition, 1995 under "Hammett Gleichung".

Preferred polar functional substituents for use in the present invention as described include, but are not limited to, polyoxyalkylene (polyether), primary and secondary amine, amide, quaternary ammonium, carboxyl, sulfonate, sulfate, carbohydrate, phosphate, and hydroxyl. More preferably, the polar functional substituents of the present invention include, but are not limited to polyoxyalkylene, primary and secondary amine, amide and carboxyl.

Suitable functionalized silicones according to the present invention include, but are not limited to, organomodified silicones with amine functionality available commercially under the trade names such as ADM1100 and ADM1600 from Wacker Silicones, DC2-8211, DC8822, DC8822A, DC8803, DC2-8040, DC2-8813, DC2-8630 and DC8566 from Dow Corning Corporation, KF-862, KF-861, KF-862S, KF-8005, KF-8004, KF-867S, KF-873, and X-52-2328 from Shin-Etsu Corporation, and TSF 4702, TSF 4703, TSF 4704, TSF 4705, TSF 4707, TSF 4708, TSF 4709, F42-B3115, SF 1708, SF 1923, SF 1921, SF 1925, OF TP AC3309, OF 7747, OF-NH TP AI3631, OF-NH TP AI3683 from GE Bayer Silicones and organomodified silicones with amine and polyether functionality available commercially under the trade names such as XS69-B5476 from GE Bayer Silicones and Abilsoft AF100 from Goldschmidt.

Preferred polar functional substituents for inclusion within the functionalized silicone contain at least one class of oxygen containing polar functional substituent, such that the oxygen content (% oxygen) within the summation of the one or more polar functional substituents (not including the oxygen in the PDMS backbone) is from 1% to 17%, preferably from 2% to 15%, and more preferably from 3% to 13% of the weight of the functionalized silicone. In addition, the hydrophilic functional silicone components of the present invention should have a silicone content (% silicone) of from 45 to 95%, preferably from 50 to 90%, and more preferably from 55 to 85% of the weight of the functionalized silicone. The silicone content or calculated percent silicone (% silicone) is defined as the average molecular weight of the PDMS backbone (consisting of silicon, oxygen and any directly attached methyl groups) divided by the average molecular weight of the whole polymer. Similarly, the overall oxygen content (% oxygen) is defined as the molecular weight of each oxygen atom multiplied by the average number of oxygen atoms present on the silicone and then divided by the average molecular weight of the whole polymer.

More preferably, the functionalized silicone polymer comprises polyoxyalkylene substituents. The polyoxyalkylene content (% polyether) should be from 5 to 55%, preferably from 10 to 50%, and more preferably from 15 to 45%. Preferably, the sum of % silicone and % polyether does not total 100%, other constituents, such as amine and amide making up the balance. The silicone content is defined above and the polyether content (% polyether) is defined as the molecular weight of each polyether pendant or block multiplied by the average number of pendants or blocks and divided by the average molecular weight of the whole polymer. If the pendant or block polyether comprises of both ethylene oxide (EO) and propylene oxide (PO) units, then this % polyether comprises the summation of % EO and % PO. If the pendant or block polyether is comprised of either only EO or only PO units, this % polyether is equivalent to the % EO or % PO, respectively.

More preferably still, the functionalized silicone is according to the following formula (I):

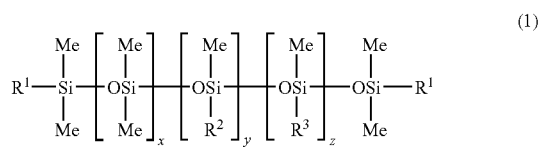

where Me equals methyl; $R^1$ is methyl or $R^2$ or $R^3$; $R^2$ is —$(CH_2)_a$—NH—$[(CH_2)_a$—NH$]_b$—H; and $R^3$ is —$(CH_2)_a$—$(OC_2H_4)_m$—$(OC_3H_6)_n$-OZ; wherein x is about 50 to 1500, y is about 1 to 20, z is about 1 to 20; a is about 2 to 5, preferably 2 to 4; b is 0 to 3, preferably 1; m is about 1 to 30; n is about 1 to 30, and Z is H, an alkyl group with 1-4 carbons, or an acetyl group, with the proviso that when y is 0, $R^1$ is an $R^2$ group, and when z is 0, $R^1$ is an $R^3$ group.

The pendant organomodified silicones comprising amino and polyoxyalkylene groups of the average formula (1) can be prepared by methods known to those skilled in the art, via steps including known polymerisation reactions (e.g. equilibration or polycondensation) and known methods of introducing organic substitution to the silicone backbone (e.g. hydrosililation).

The following are non-limiting exemplary structures of the functionalized silicone according to the present invention.

Material A

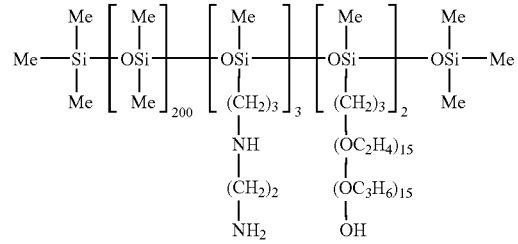

In Example A, molecular weight=18738; % oxygen=5.21% (contributed by thirty one oxygen atoms); and

| % silicone = | 81.42% |
|---|---|
| % polyether = | 16.33% |
| % other* = | 2.25% |
| | 100.00% |

*contributed by other side chain and the —$(CH_2)_3$— and —OH moieties on the polyether side chain.

Material B

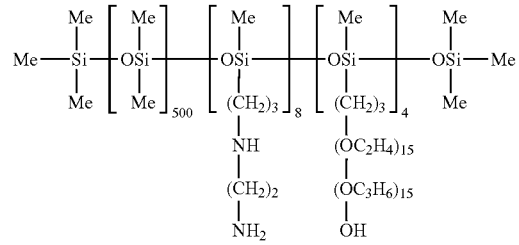

Material C

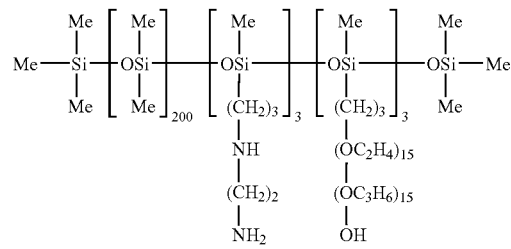

Material D

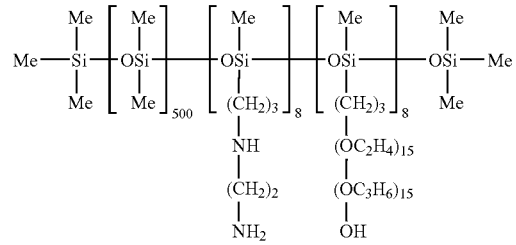

Preferably, the durability additive according to the invention comprises one or more organosiloxane resins.

Without wishing to be bound by theory, organosiloxane resins are believed to create a 3-dimensional network within the functionalized silicone fluid giving rise to vicoelasticity thereby improving the adhesive properties of the fluid and hence the durability on a fibrous substrate. Preferably, the organosiloxane resin is insoluble in water. In the case that the fiber treatment composition is an emulsion, the mixture of the functionalized silicone and the organosiloxane resin may be dispersed therewithin in the form of emulsified droplets.

Organosiloxane resins which my be included in the durability additive according to the invention comprise combinations of $R_3SiO_{1/2}$ "M" units, $R_2SiO$ "D" units, $RsiO_{3/2}$ "T" units, $SiO_2$ "Q" units in ratios to each other that satisfy the relationship $R_nSiO_{(4-n)/2}$ where n is a value between 1.0 and 1.50 and R is a methyl group. Silanol or alkoxy functionalities may also be present in the resin structure.

More preferably, the organosiloxane resins comprise repeating monofunctional $R_3SiO_{1/2}$ "M" units and the quadrafunctional $SiO_2$ "Q" units, otherwise known as "MQ" resins. In this case, the ratio of the "M" to "Q" functional units is advantageously from 0.7 and the value of n is 1.2. Organosiloxane resins such as these are commercially available as SR1000 available from GE Bayer Silicones and Wacker 803 from Wacker Silicones.

Advantageously, the organosiloxane resins according to the invention are solid at about 25° C. and have a molecular weight range of from 1,000 to 10,000 grams/mole.

Reference is made to Table 2, which demonstrates the improvement in durability that may be achieved by adding MQ resin to some commercially available functionalized silicones:

TABLE 2

| Silicone | Durability on chemically damaged hair (%) |
|---|---|
| Silicone Z[1] | 0 |
| Silicone Z[1] + 1% MQ resin[2] | 0 |
| Silicone Z[1] + 5% MQ resin[2] | 19 |
| Silicone Z[1] + 10% MQ resin[2] | 24 |
| XS69-B5476[4] | 7 |
| XS69-B5476[4] + 0.5% MQ resin[2] | 9 |
| XS69-B5476[4] + 1% MQ resin[2] | 13 |
| XS69-B5476[4] + 2% MQ resin[2] | 19 |
| XS69-B5476[4] + 10% MQ resin[2] | 19 |
| DC-2-8566[3] | 11 |
| DC-2-8566[3] + 0.05% MQ resin[2] | 52 |
| Rhodorsil 21637[5] | 2 |
| Rhodorsil 21637[5] + 0.5% MQ resin[2] | 52 |
| Rhodorsil 21637[5] + 1.0% MQ resin[2] | 100 |

[1]Silicone Z is an aminosilicone with an average of 110 D units and two terminal aminopropyl functional groups
[2]Available as SR1000 from GE silicones
[3]Available as DC-2-8566 from Dow Corning
[4]Available as XS69 B5476 from GE silicones
[5]Available as Rhodorsil 21637 from Rhodia The fiber treatment composition according to the invention is advantageously a hair treatment composition. In such a case, the composition may additionally comprise a hair bleaching component and/or a hair dyeing component.

According to a further aspect of the invention, a hair treatment kit is provided comprising:
(a) an oxidative bleaching composition
(b) a dye composition a hair treatment composition as defined hereinabove comprised within component (a) and/or within component (b) and/or provided as a separate component.

The fiber treatment composition according to the present invention may include a cosmetically acceptable vehicle to act as a diluent, dispersant, or carrier for the silicone oil in the composition, so as to facilitate the distribution of the silicone oil when the composition is applied. The vehicle may be an aqueous emulsion, water, liquid or solid emollients, solvents, humectants, propellants, thickeners and powders.

Advantageously, the fiber treatment compositions according to the present invention may be in the form an emulsion with water as a primary component, although aqueous organic solvents, may also be included. The emulsion may be a water-in-oil emulsion, an oil-in-water emulsion, a water-in-oil-in-water multiple emulsion, or an oil-in-water-in-oil multiple emulsion, but is preferably an oil-in-water emulsion (a silicone-in-water emulsion).

The aqueous continuous phase of the emulsion treatment compositions of the present invention may further comprise an emulsifier to facilitate the formation of the emulsion. Emulsifiers for use in the aqueous continuous phase of the present emulsion treatment compositions may include an anionic surfactant, cationic surfactant, amphoteric surfactant, water-soluble polymeric surfactant, water-soluble silicone-containing surfactant, nonionic surfactant having an HLB of greater than about 10, or a surfactant system capable of forming stabilizing liquid crystals around the silicone droplets. The nonionic surfactant preferably has an HLB of at least 12, and more preferably, an HLB value of at least about 15. Surfactants belonging to these classes are listed in *McCutcheon's Emulsifiers and Detergents, North American and International Editions*, MC Publishing Co., Glen Rock N.J., pages 235-246 (1993).

The emulsifier for the aqueous phase does not gel the aqueous phase. The emulsifier may, however, be capable of forming a stabilizing layer of lamellar liquid crystals around silicone droplets. This barrier film prevents coalescence between emulsion droplets. In this case, the surfactant system may be a single surfactant or a blend of surfactants. In some cases, a particular surfactant cannot form a liquid crystal structure alone, but can participate in the formation of liquid crystals in the presence of a second surfactant. Such a surfactant system forms a layer of lamellar liquid crystals around the silicone to provide a barrier between the silicone and the aqueous phase. This type of an emulsion is different from the conventional emulsions, which rely upon the orientation of the hydrophobic and hydrophilic components of a surfactant at an silicone-water interface. The formation of a layer of lamellar liquid crystals around the silicone can be detected by the presence of Maltese crosses viewed by optical microscopy through crossed polarizing plates or by freeze fracture electron microscopy.

Exemplary classes of surfactants capable of participating in the formation of a liquid crystal structure around the silicone droplets include, but are not limited to specific cationic surfactants, anionic surfactants, nonionic surfactants, quaternary ammonium surfactants and lipid surfactants.

Specific nonionic surfactants are fatty alcohols or fatty acids, or derivatives thereof, or a mixture of any of these, having a chain length of from about 14 to about 20 carbon atoms. These materials may be predominantly linear or may be branched. Some examples include myristyl alcohol, myristic acid, cetyl alcohol, palmitic acid, cestearyl alcohol, stearyl alcohol, stearic acid, oleic acid, oleyl alcohol, arachidyl alcohol, arachidic acid, and mixtures thereof.

Other specific non-ionic surfactants include condensation products of aliphatic ($C_{16}$ to $C_{22}$) primary or secondary linear or branched chain alcohols or phenols with alkylene oxides, usually ethylene oxide, and generally having from 1 to 30 ethylene oxide groups. Some examples include, but are not limited to, ceteth-1, ceteth-2, ceteth-3, ceteth-4, ceteth-5, ceteth-6, ceteth-10, ceteth-12, ceteth-14, ceteth-15, ceteth-16, ceteth-20, ceteth-24, ceteth-25, ceteth-30, ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, steareth-2, steareth-3, steareth-4, steareth-5, steareth-6, steareth-7, steareth-8, steareth-10, steareth-11, steareth-13, steareth-14, steareth-15, steareth-16, steareth-20, steareth-21, steareth-25, steareth-27, steareth-30, arachideth-20, beheneth-5, beheneth-10, beheneth-20, beheneth-25, beheneth-30 and mixtures thereof.

Specific cationic surfactants include quaternary ammonium halides, e.g., alkyltrimethylammonium halides in which the alkyl group has from about 12 to 22 carbon atoms, for example dodecyltrimethyl-ammonium chloride, hexadecyltrimethylammonium chloride, cetyltrimethylammonium chloride, behenyltrimethylammonium chloride, benzyltrimethylammonium chloride, octyldimethylbenzyl-ammonium chloride, decetyldimethylbenzylammonium chloride, stearyldimethylbenzylammonium chloride, distearyldimethylammonium chloride, didodecyldimethylammonium chloride, dioctadecyldimethylammonium chloride, tallow trimethylammonium chloride, cocotrimethyl-ammonium chloride, cetylpyridinium chloride and their other corresponding halide salts and hydroxides. Preferred cationic surfactants are cetyltrimethylammonium chloride (CTAC) and cetyltrimethylammonium bromide (CTAB 99% from Fluka, CTAC 50% (Arquad 16-50, Akzo). Preferably, cationic surfactants are used at 2-10% with CTAC and CTAB being the preferred cationic surfactants. Additionally, when monoalkyl substituted cationic surfactants are used, it is preferred to also employ cholesterol wherein the ratio of cholesterol to cationic surfactant ranges from 0.1:1.0 to 1.0:1.0, more preferably from 0.5:1.0 to 1.5:1.0, and most preferably 0.7:1.0 to 1.25:1.0.

Specific anionic surfactants are di-alkyl sulfonates, di-alkyl ether sulfonates, di-alkylaryl sulfonates, di-alkanoyl isethionates, di-alkyl succinates, di-alkyl sulfosuccinates, di-N-alkoyl sarcosinates, di-alkyl phosphates, di-alkyl ether phosphates, di-alkyl ether carboxylates, and di-alpha-olefin sulfonates, especially their sodium, magnesium, ammonium and mono-, di- and triethanolamine salts. The alkyl and acyl groups generally contain from 12 to 20 carbon atoms and may be unsaturated.

The stabilizing liquid crystals may also be formed from lipid surfactants including either phospholipids, i.e., based on glycerol and sphingosine, or glycolipid, i.e. based on sphingosine. Phospholipids are preferred with phosphatidyl choline (lecithin) being the preferred phospholipid. Of the alcohol moieties which comprise the phosphoglycerides, serine, choline and ethanolamine are particularly preferred, and of the fatty chains, those having a chain length of $C_{14}$ to $C_{24}$ are preferred. The fatty acid chains may be branched or unbranched, saturated or unsaturated, and palmitic, myristic, oleic, stearic, arachidonic, linolenic, linoleic and arachidic acids are particularly preferred.

Preferred surfactants for the formation of liquid crystals in the aqueous continuous phase are of the nonionic type and include $C_{16-22}$ fatty alcohols, and $C_{16-22}$ fatty alcohol ethoxylates with 1 to 30 ethylene oxide groups. Specific examples include cetearyl alcohol, cetyl alcohol, stearyl alcohol, arachidyl alcohol, oleyl alcohol, ceteareth ethoxylates with between 10 and 30 ethylene oxide groups, ceteth ethoxylates with between 10 to 30 ethylene oxide groups, steareth ethoxylates with between 10 and 30 ethoxylates, and combinations thereof. Preferably, $C_{16-22}$ fatty alcohols are used in combination with $C_{16-22}$ fatty alchol ethoxylates at a ratio of between 10:1 to 0.5:1, more preferably between 6:1 and 1:1, and most preferably between 5:1 and 1.5:1.

The aqueous continuous phase should ideally comprise the emulsifier in an amount sufficient to stabilize the silicone. In one embodiment, the aqueous continuous phase comprises the emulsifier in an amount of from about 0.1% to about 15%, and more preferably from about 0.1% to about 10%, based on the weight of the aqueous continuous phase.

The composition according to the present application finds particular utility in hair coloring compositions especially oxidative hair colorants wherein the hair is subjected to a particularly aggressive environment.

A preferred hair coloring agent for use herein is an oxidative hair coloring agent. The concentration of each oxidative hair coloring agent in the compositions according to the present invention may be from about 0.0001% to about 5% by weight.

Any oxidative hair coloring agent can be used in the compositions herein. Typically, oxidative hair coloring agents comprise at least two components, which are collectively referred to as dye forming intermediates (or precursors). Dye forming intermediates can react in the presence of a suitable oxidant to form a colored molecule.

The dye forming intermediates used in oxidative hair colorants include: aromatic diamines, aminophenols, various heterocycles, phenols, napthols and their various derivatives. These dye forming intermediates can be broadly classified as; primary intermediates and secondary intermediates. Primary intermediates, which are also known as oxidative dye precursors, are chemical compounds which become activated upon oxidation and can then react with each other and/or with couplers to form colored dye complexes. The secondary intermediates, also known as color modifiers or couplers, are generally colorless molecules which can form colors in the presence of activated precursors/primary intermediates, and are used with other intermediates to generate specific color effects or to stabilise the color.

Primary intermediates suitable for use in the compositions and processes herein include: aromatic diamines, polyhydric phenols, amino phenols and derivatives of these aromatic compounds (e.g., N-substituted derivatives of the amines, and ethers of the phenols). Such primary intermediates are generally colorless molecules prior to oxidation.

While not wishing to be bound by any particular theory, it is believed that the process by which color is generated from these primary intermediates and secondary coupler compounds generally includes a stepwise sequence whereby the primary intermediate can become activated (by oxidation), and then enjoins with a coupler to give a dimeric, conjugated colored species, which in turn can enjoin with another 'activated' primary intermediate to produce a trimeric conjugated colored molecule.

In general terms, oxidative dye primary intermediates include those materials which, on oxidation, form oligomers or polymers having extended conjugated systems of electrons in their molecular structure. Because of the new electronic structure, the resultant oligomers and polymers exhibit a shift in their electronic spectra to the visible range and appear colored. For example, oxidative primary intermediates capable of forming colored polymers include materials such as aniline, which has a single functional group and which, on oxidation, forms a series of conjugated imines and quinoid dimers, trimers, etc. ranging in color from green to black. Compounds such as p-phenylenediamine, which has two functional groups, are capable of oxidative polymerization to yield higher molecular weight colored materials having extended conjugated electron systems. Oxidative dyes known in the art can be used in the compositions according to the present invention. A representative list of primary intermediates and secondary couplers suitable for use herein is found in Sagarin, "Cosmetic Science and Technology", Interscience, Special Ed. Vol. 2 pages 308 to 310.

The primary intermediates can be used alone or in combination with other primary intermediates, and one or more can be used in combination with one or more couplers. The choice of primary intermediates and couplers will be determined by the color, shade and intensity of coloration which is desired. There are nineteen preferred primary intermediates and couplers which can be used herein, singly or in combination, to provide dyes having a variety of shades ranging from ash blonde to black; these are: pyrogallol, resorcinol, p-toluenediamine, p-phenylenediamine, o-phenylenediamine, m-phenylenediamine, o-aminophenol, p-aminophenol, 4-amino-2-nitrophenol, nitro-p-phenylenediamine, N-phenyl-p-phenylenediamine, m-aminophenol, 2-amino-3-hydroxypyridine, 1-napthol, N,N bis(2-hydroxyethyl)$_p$-phenylenediamine, resourcinol, diaminopyrazole, 4-amino-2-hydroxytoluene, 1,5-dihydroxynapthalene, 2-methyl resorcinol and 2,4-diaminoanisole. These can be used in the molecular form or in the form of peroxide-compatible salts.

The hair coloring compositions of the present invention may, in addition to or instead of an oxidative hair coloring agent, include non-oxidative and other dye materials. Optional non-oxidative and other dyes suitable for use in the hair coloring compositions and processes according to the present invention include both semi-permanent, temporary and other dyes. Non-oxidative dyes as defined herein include the so-called 'direct action dyes', metallic dyes, metal chelate dyes, fiber reactive dyes and other synthetic and natural dyes. Various types of non-oxidative dyes are detailed in: 'Chemical and Physical Behaviour of Human Hair' 3rd Ed. by Clarence Robbins (pp 250-259); 'The Chemistry and Manufacture of Cosmetics'. Volume IV. 2nd Ed. Maison G. De Navarre at chapter 45 by G. S. Kass (pp 841-920); 'cosmetics: Science and Technology' 2nd Ed., Vol. II Balsam Sagarin, Chapter 23 by F. E. Wall (pp 279-343); 'The Science of Hair Care' edited by C. Zviak, Chapter 7 (pp 235-261) and .'Hair Dyes', J. C. Johnson, Noyes Data Corp., Park Ridge, U.S.A. (1973), (pp 3-91 and 113-139).

The hair coloring compositions herein preferably comprise at least one oxidising agent, which may be an inorganic or organic oxidising agent. The oxidising agent is preferably present in the coloring composition at a level of from about 0.01% to about 10%, preferably from about 0.01% to about 6%, more preferably from about 1% to about 4% by weight of the composition.

A preferred oxidising agent for use herein is an inorganic peroxygen oxidising agent. The inorganic peroxygen oxidising agent should be safe and effective for use in the present compositions. Preferably, the inorganic peroxygen oxidising agents suitable for use herein will be soluble in the compositions according to the present invention when in liquid form or in the form intended to be used. Preferably, inorganic peroxygen oxidising agents suitable for use herein will be water-soluble. Water soluble oxidising agents as defined herein means agents which have a solubility to the extent of about 10 g in 1000 ml of deionised water at 25° C. ("Chemistry" C. E. Mortimer. 5th Edn. p 277).

The inorganic peroxygen oxidising agents useful herein are generally inorganic peroxygen materials capable of yielding peroxide in an aqueous solution. Inorganic peroxygen oxidising agents are well known in the art and include hydrogen peroxide, inorganic alkali metal peroxides such as sodium periodate, sodium perbromate and sodium peroxide, and inorganic perhydrate salt oxidising compounds, such as the alkali metal salts of perborates, percarbonates, perphosphates, persilicates, persulphates and the like. These inorganic perhydrate salts may be incorporated as monohydrates, tetrahydrates etc. Mixtures of two or more of such inorganic peroxygen oxidising agents can be used if desired. While alkali metal bromates and iodates are suitable for use herein the bromates are preferred. Highly preferred for use in the compositions according to the present invention is hydrogen peroxide.

The compositions herein may instead or in addition to the inorganic peroxygen oxidising agent(s), comprise one or more preformed organic peroxyacid oxidising agents.

Suitable organic peroxyacid oxidising agents for use in the coloring compositions according to the present invention have the general formula:

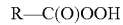

wherein R is selected from saturated or unsaturated, substituted or unsubstituted, straight or branched chain, alkyl, aryl or alkaryl groups with from 1 to 14 carbon atoms.

The organic peroxyacid oxidising agents should be safe and effective for use in the compositions herein. Preferably, the preformed organic peroxyacid oxidising agents suitable for use herein will be soluble in the compositions used according to the present invention when in liquid form and in the form intended to be used. Preferably, organic peroxyacid oxidising agents suitable for use herein will be water-soluble. Water-soluble preformed organic peroxyacid oxidising agents as defined herein means agents which have a solubility to the extent of about 10 g in 1000 ml of deionised water at 25° C. ("Chemistry" C. E. Mortimer. 5th Edn. p 277).

The compositions herein may optionally contain a transition metal containing catalyst for the inorganic peroxygen oxidising agents and the optional preformed peroxy acid oxidising agent(s). Suitable catalysts for use herein are disclosed in WO98/27945.

The compositions herein may contain as an optional component a heavy metal ion sequestrant. By heavy metal ion sequestrant it is meant herein components which act to sequester (chelate or scavenge) heavy metal ions. These components may also have calcium and magnesium chelation capacity, but preferably they show selectivity to binding heavy metal ions such as iron, manganese and copper. Such sequestering agents are valuable in hair coloring compositions as herein described for the delivery of controlled oxidising action as well as for the provision of good storage stability of the hair coloring products.

Heavy metal ion sequestrants may be present at a level of from about 0.005% to about 20%, preferably from about 0.01% to about 10%, more preferably from about 0.05% to about 2% by weight of the compositions.

Suitable sequestering agents are disclosed in WO98/27945.

For use, the treatment compositions according to an embodiment of the invention may be provided at a pH from about 3 to 11, preferably from 4 to 10.5.

The present compositions do not only find application in the treatment of fibers, such as hair, but may also be applied to other substrates, such as human skin, nails and various animal body parts, such as horns, hooves and feathers.

Test Methods

Hydrophilicity Index Method:

The hydrophilicity indexes were measured via turbidimetry on an LP2000 Turbidity Meter from Hanna Instruments, Bedfordshire, United Kingdom.

A 100 ml beaker is thoroughly cleaned, including prior rinsing with hexane then ethanol, and then dried:

1. 0.3500 grams (+/−0.0015 g) of the functionlized silicone is weighed directly into the beaker.
2. 24.6500 grams (+/−0.0500 g) of ethanol (ethyl alcohol, 99.7% vol/vol minimum, A.R. quality, EEC No. 200-578-6) is then weighed directly into the beaker.
3. The contents of the beaker is then mixed thoroughly via a high shear mixer (IKA Labortechnik—Ultra—Turrax T8 from IKA Werke GmbH & Co. KG, Staufen, Germany) for 1 minute with special attention to ensure the silicone is completely removed from the bottom of the beaker and thereby mixed properly.
4. Immediately dispense using a pipette, 10 ml of the resulting liquid into a clean cuvette (Note: The cuvette is thoroughly rinsed with hexane twice, then rinsed with ethanol twice and then dried prior to readings) which is then loaded into the turbidity meter.
5. After approximately 30 seconds a turbidity reading is recorded, immediately followed by a second reading for verification.
6. Steps 1-5 are repeated 3 times, the turbidity values being averaged to give the average turbidity reading for the functionalized silicone.

The hydrophilicity index for the functionalized silicone is then computed as follows:

Hydrophilicity Index=100−((Average turbidity)/400)×100

Interfacial Tension Measurement Protocol

The silicone/water interfacial tensions of the organomodified silicones were measured via pendant drop shape analysis on a Kruss DSA-10 instrument as taught in F. K. Hansen, G. Rodsrun, "Surface tension by pendant drop. A fast standard instrument using computer image analysis", Journal of Colloid and Interface Science, Volume 141, Issue 1, January 1991, pages 1-9. The accuracy of this method is dependent upon the density difference between the reference fluid (usually water) and the test fluid. Given that many of the present functionalized silicones have densities approaching that of water, $D_2O$ (with a density of 1.1 $g/cm^{-3}$) was substituted for $H_2O$ as the more dense phase, in order to ensure a sufficient density difference. The respective densities of the organomodified silicones were measured with a Calculating Precision Density Meter DMA 55 instrument from Apollo Scientific Limited.

Viscosity of Functionalized Silicone Fluids—Measurement Protocol

An AR 500 rotational rheometer (TA Instruments Ltd., Leatherhead, Surrey KT22 7UQ, UK) is used to determine the viscosity of the functionalized silicone fluids used herein. The determination is performed at 30° C., with the 4 cm 2° steel cone measuring system set with a 49 μm (micron) gap and is performed via the programmed application of a shear stress of 0.5 to 590 Pa over a 2 minute time period. These data are used to create a shear rate vs. shear stress curve for the material. This flow curve can then be modelled in order to provide a material's viscosity. These results were fitted with the following well-accepted Newtonian model:

Viscosity, $\mu = \sigma/\gamma$ (where $\sigma$ is shear stress; $\gamma$ is shear rate)

Silicone Durability Method

Hair Substrate Preparation Method

Durability is only assessed on a polar, chemically damaged hair substrate. Hair is supplied by Hugo Royer International Limited (10 Lakeside Business Park, Sandhurst, Berkshire, GU47 9DN, England) and is a blended, Eastern European, mid-brown human hair. Prior to use, the hair is assessed and qualified for low cuticular damage (<20%) and misalignment (<5%), based on at least 200 hair strands per batch. Any damage on a hair strand counts as one point damaged, and then the total is calculated as a percentage. This hair is made into 4″ (10 cm), 2 g round tied switches (where the length and weight of hair corresponds to the hair below the tie).

Hair switches are chemically damaged using the following two component bleaching formulations:

| Ingredients | Wt/Wt % |
|---|---|
| Peroxide base | |
| 1. Emulsion base: | |
| | |
| Deionized water | 29.78 |
| Cetyl alcohol (1) | 2.24 |
| Stearyl alcohol (2) | 2.24 |
| Ceteareth-25 (3) | 1.50 |
| Phenoxyethanol (4) | 0.11 |
| Sodium benzoate (5) | 0.09 |
| Tetrasodium EDTA (87%) (6) | 0.04 |
| 2. Chelant premix | |
| | |
| Deionized water | 35.72 |
| Pentasodium pentetate (40%) (7) | 0.24 |
| Hydroxyethane diphosphonic acid (60%) (8) | 0.16 |
| Phosphoric acid (75%) (9) | 0.08 |
| Sodium stannate (95%) (10) | 0.04 |
| 3. Peroxide mix | |
| | |
| Hydrogen peroxide (35%) (11) | 17.15 |
| Deionized water | 10.61 |
| Carrier base for dye base | |
| 1. Acetic acid pre-mix | |
| | |
| Deionized water | 46.49 |
| Acetic acid (50%) (12) | 3.91 |
| 2. Emulsion base | |
| | |
| Deionized water | 29.78 |
| Cetyl alcohol (1) | 2.24 |
| Stearyl alcohol (2) | 2.24 |
| Ceteareth-25 (3) | 1.50 |
| Phenoxyethanol (4) | 0.11 |
| Sodium benzoate (5) | 0.09 |
| Tetrasodium EDTA (87%) (6) | 0.04 |
| Ammonium hydroxide (13) | 13.60 |

(1): available as Surfac cetyl alcohol from Surfachem, Leeds, UK
(2): available as Surfac stearyl alcohol from Surfachem, Leeds, UK
(3): available as Volpo CS25 from Croda, North Humberside, UK
(4): available as Phenoxyethanol from Nipa-Hardwicke, Wilmington, Delaware
(5): available as Sodium benzoate EP/USP from Haltermann, Cumbria, UK
(6): available as Edeta B powder from BASF, Cheadle, Cheshire, UK
(7): available as Trilon C liquid from BASF, Cheadle, Cheshire, UK
(8): available as Dequest 2010 from Solutia, Newport, South wales
(9): available as Phosphoric acid 750F from Albright & Wilson, West Midlands, UK
(10): available as Sodium stannate, Aldrich
(11): available as Hydrogen peroxide 35% 171/4 from Ellis & Everard, Walsall, UK
(12): available as 50% acetic acid from Hays, Greenwich, London, UK
(13): available as Ammonium Solution BP grade from Brotherton Speciality Products, West Yorkshire, UK These products are made using the following protocols:

Peroxide Base:

The first stage is to make the emulsion base; this is prepared by adding to a vessel deionized water and commencing agitation, and then heating to 82° C. Then tetrasodium EDTA and sodium benzoate are added and dissolved, followed by addition of ceteareth25, cetyl alcohol and stearyl alcohol. During the addition process the temperature is maintained above 80° C., finally phenoxyethanol is added, the mixture is then homogenized for 30 min. The emulsion structure is obtained by cooling whilst still high shear mixing the product down below 50° C. The emulsion base is then left to thicken for 60 min.

The chelants are added to the deionised water with mixing to form the chelant premix. This is then added with stirring to the pre-made emulsion base. Adding the peroxide mix water followed by hydrogen peroxide to the emulsion base/chelant premix and stirring until homogeneous makes the completed peroxide base.

Carrier Base for Dyes

The carrier base for dyes is prepared by adding water to a vessel and commencing agitation, followed by the addition of acetic acid, then by the emulsion base (see emulsion base preparation described hereinbefore for the peroxide base). When fully mixed, ammonium hydroxide is added to the mixture and the stirring continued until the product is homogenous.

Equal weights of the two components, the peroxide base and carrier base for dyes are mixed together thoroughly to produce the bleaching system. To each dry untreated hair switch, 4 g of this bleaching system is then applied, and thoroughly worked into the hair, using the fingers, to ensure even, complete, coverage. The hair switch is then wrapped in cling film and incubated in an oven at 30° C. for 30 minutes, after which the product is rinsed for 2 minutes (in a sink fitted with a shower attachment set with a flow rate of 6±1 L min$^{-1}$ and a temperature of 37±2° C.) with finger agitation. Finally the switches are dried using a hot air drier (Babyliss Lightweight Professional model 1015 (1400 W) for 3 min. The bleached hair switches are then washed in a sink fitted with a shower attachment set with a flow rate of 6±1 L min$^{-1}$ and a temperature of 37±2° C. Switches are initially wetted under the shower attachment for 30 s. The hair is then removed from the water flow and 0.2 g of shampoo (Pantene Pro-V Clarifying Shampoo) is applied down each switch, and then lathered for 30 s by hand before rinsing for 60 s under the shower. The hair is again removed from the shower, and has a further 0.2 g of shampoo applied, and lathered for 30 s before finally rinsing under the shower for 60 s. Hair switches are then dried using a hot air drier (Babyliss Lightweight Professional model 1015 (1400 W) for 3 min. This washing protocol comprising two shampoo applications and one drying step is defined as a single wash cycle. This washing method is then repeated again through another complete wash cycle. The dry hair switches are then bleached again according to the method outlined above and subsequently washed again through two complete wash cycles. This hair is hereinafter defined as "damaged" hair and is hereafter used a hydrophilic hair substrate.

Hair Treatment

The functionalised silicone under investigation for durability is prepared for assessment using the following method. The functionalised silicone polymer is pre-mixed with the durability additive until homogeneous. To deliver the silicone/additive mixture, a matrix comprising 36 wt. % of the "emulsion base", described hereinbefore for use in the preparation of the damaged hair substrate, obtained primarily through dilution with water, but also optionally comprising hydrogen peroxide and ammonium hydroxide, is used. Within the matrix, 1.75% of the silicone/additive under investigation is thoroughly dispersed using conventional techniques. A sufficient amount of product is applied to four chemically damaged hair switches for a sufficient time to provide an initial deposition above 100 ppm. The hair is then rinsed to remove the matrix (in a sink fitted with a shower attachment set with a flow rate of 6±1 L min$^{-1}$ and a temperature of 37±2° C.) with finger agitation. The switches are dried using a hot air drier (Babyliss Lightweight Professional model 1015 (1400 W) for 3 min.

When the switches are dry they are split into two groups both comprising equal numbers of damaged hair switches. The first are used to measure the initial deposition. The second set is washed to assess the silicone durability. The hair switches are washed in a sink fitted with a shower attachment set with a flow rate of 6±1 L min$^{-1}$ and a temperature of 37±2° C. Switches are initially wetted under the shower attachment for 30 s. The hair is removed from the water flow and 0.2 g of shampoo ("Pantene Classic Clean Shampoo") is applied along each switch, and then lathered for 30 s by hand before rinsing for 60 s under the shower. The switch then has a further 0.2 g of shampoo application, and is lathered for 30 s before finally rinsing under the shower for 60 s. Hair switches are then dried using a hot air drier (Babyliss Lightweight Professional model 1015 (1400 W) for 3 min. This protocol comprising two shampoo applications and one drying step is defined as one complete wash cycle. This washing protocol is then repeated again through another eleven complete cycles (to make twelve wash cycles in total). These switches are then measured for silicone deposition to assess the durability performance.

Silicone Deposition Measurement

A wavelength dispersive X-Ray Fluoresence spectrometer (Phillips Electronics, PW2404 Sequential "4000W" X-Ray Spectrometer System) is utilised to determine the silicone deposition level on hair. The spectrometer is fitted with a Rhodium tube and includes an InSb crystal to facilitate high sensitivity silicone detection.

Characteristic x-ray photons are produced from the ejection of an inner shell electron of an silicone atom followed by a transition of an electron from a higher energy state to the empty inner shell. X-ray fluorescence of silicone in polydimethylsiloxane (PDMS) is directly proportional to the amount of PDMS deposited on the hair. A critical component to facilitate the use of XRF technology is the ability to present the sample to the spectrometer in a consistent manner. The hair switch is arranged in a custom-made sample holder, which presents a continuous, flat, aligned hair surface across the exposed sample area (16 mm diameter). The sample is analysed under a helium atmosphere using a Tube voltage of 32 kV and current of 125 mA, with an irradiation/acquisition time of 60 s.

The drift in the analytical signal is regularly monitored and evaluated. The preferred approach employed is to use a known standard that does not need to be prepared each time the drift is assessed. An Ausmon sample is an appropriate monitor sample for many applications, including silicon determinations. A drift correction with the Ausmon sample for silicon is performed at the beginning of each day samples are analyzed. The calculated drift is below 3% between sets of analysis.

Calculation of the amount of silicon on hair in units of ppm from can be made with equation 1.

$$x_2 = (I - b_1)/m_1 \qquad (1)$$

Where $m_1$ and $b_1$ are calculated from a calibration curve constructed from measurements of the XRF signal as a function of the amount of silicone deposited on hair subsequently assayed using atomic absorption on the extracted silicone.

To translate the XRF silicone deposition data obtained as hereinbefore described into a measure of silicone durability, it is necessary to generate a silicone durability index value. To generate the silicone durability index value the following equation is employed:

$$\text{Silicone durability index value (\%)} = \frac{Dep(12\text{cycle})}{Dep(\text{initial})} \times 100$$

Where Dep(initial) equals the XRF deposition value obtained on hair after silicone deposition with no washing cycles, Dep(12 cycles) equals the XRF deposition value obtained on hair after silicone deposition and subsequent 12 wash cycles.

Viscoelasticity Measurement of the Functionalized Silicone Fluids

The AR 500 rotational Rheometer (TA Instruments) is used to determine the G' and G" of the functional silicone fluids used herein. The determination is performed at 25° C., with the 6 cm acryllic parrellel plate measuring system set with a 100 micron gap and is performed via the programmed application of a oscillatory stress of 2 Pa over a oscillation frequency range of 1 to 40 Hz. This data is used to determine the ratio of G' to G". A minimum of 30 data points is recorded over a linear frequency ramp. These data is used to determine the mean ratio of G' to G" between 20 and 40 Hz.

EXAMPLES

The following examples further describe and demonstrate the preferred embodiments within the scope of the present invention. The examples are given solely for the purpose of illustration, and are not to be construed as limitations of the present invention since many variations thereof are possible without departing from its scope.

Examples 1-4

Colorant Compositions

| Ingredients | #1 Wt % | #2 Wt % | #3 Wt % | #4 Wt % |
|---|---|---|---|---|
| Peroxide base | | | | |
| Emulsion base: | | | | |
| Deionized water | 29.17 | 29.17 | 29.17 | 29.17 |
| Cetyl alcohol (1) | 2.20 | 2.20 | 2.20 | 2.20 |
| Stearyl alcohol (2) | 2.20 | 2.20 | 2.20 | 2.20 |
| Ceteareth-25 (3) | 1.47 | 1.47 | 1.47 | 1.47 |
| Phenoxyethanol (4) | 0.11 | 0.11 | 0.11 | 0.11 |
| Sodium benzoate (5) | 0.09 | 0.09 | 0.09 | 0.09 |
| Tetrasodium EDTA (87%) (6) | 0.04 | 0.04 | 0.04 | 0.04 |
| Deionized water | 35.00 | 35.00 | 35.00 | 35.00 |
| Pentasodium pentetate (40%) (7) | 0.24 | 0.24 | 0.24 | 0.24 |
| Hydroxyethane diphosphonic acid (60%) (8) | 0.16 | 0.16 | 0.16 | 0.16 |
| Phosphoric acid (75%) (9) | 0.08 | 0.08 | 0.08 | 0.08 |
| Sodium stannate (95%) (10) | 0.04 | 0.04 | 0.04 | 0.04 |
| Hydrogen peroxide (35%) (11) | 16.80 | 16.80 | 16.80 | 16.80 |
| Deionized water | 10.40 | 10.40 | 9.40 | 9.40 |
| Functionalized Silicone premix: | | | | |
| MQ resin sold under the name SR1000 by the company GE Bayer Silicones | 0.10 | 0.20 | 0.06 | 0.02 |
| Aminopolyether functional silicone fluid sold under the name XS69-B5476 by the company GE bayer silicones | 1.90 | | | |
| Aminofunctional polydimethylsiloxane sold under the name Rhodorsil 21645 by the company Rhodia | | 1.80 | | |
| Aminofunctional polydimethylsiloxane sold under the name DC 2-8566 silicone fluids by the company Dow corning | | | 1.94 | 1.98 |
| Carrier base for dye base | | | | |
| Deionized water | 46.49 | 46.49 | 46.49 | 46.49 |
| Acetic acid (50%) (12) | 3.91 | 3.91 | 3.91 | 3.91 |
| Emulsion base (see ingredients above) | 36.00 | 36.00 | 36.00 | 36.00 |
| Ammonium hydroxide (13) | 13.60 | 13.60 | 13.60 | 13.60 |

(1): available as Surfac cetyl alcohol from Surfachem, Leeds, UK
(2): available as Surfac stearyl alcohol from Surfachem, Leeds, UK
(3): available as Volpo CS25 from Croda, North Humberside. UK
(4): available as Phenoxyethanol from Nipa-Hardwicke, Wilmington, Delaware
(5): available as Sodium benzoate EP/USP from Haltermann, Cumbria, UK
(6): available as Edeta B powder from BASF, Cheadle, Cheshire, UK
(7): available as Trilon C liquid from BASF, Cheadle, Cheshire, UK
(8): available as Dequest 2010 from Solutia, Newport, South wales
(9): available as Phosphoric acid 750F from Albright & Wilson, West Midlands, UK
(10): available as Sodium stannate, Aldrich
(11): available as Hydrogen peroxide 35% 171/4 from Ellis & Everard, Walsall, UK
(12): available as 50% acetic acid from Hays, Greenwich, London, UK
(13): available as Ammonium Solution BP grade from Brotherton Speciality Products, West Yorkshire, UK Production of the Example Colorant Applications Peroxide Base:

The emulsion base is prepared by adding to a vessel the deionized water and commencing agitation with heating to 82° C. Then the preservatives (tetrasodium EDTA, sodium benzoate) are added and dissolved. This is followed by addition of ceteareth25, cetyl alcohol and stearyl alcohol while keeping the temperature above 80° C. Then phenoxytol is added. The mixture is then fully blended hot through a recirculation line and homogenized. The emulsion structure is obtained by cooling the product down below 50° C. and shearing while cooling. The product is left to thicken for 60 min.

The chelant premix is prepared by adding the chelants to water and mixing them together in a vessel. Then this solution is added to the emulsion base. The completed peroxide base is made by adding water to the previous mixture followed by the hydrogen peroxide while stirring.

The functionalised silicone and organosiloxane resin are pre-mixed together under agitation and then added to the peroxide base and stirred until the desired particle size is obtained.

Carrier System for Dye Base:

The carrier base is prepared by adding water to a vessel and commencing agitation, followed by the addition of acetic acid. Then emulsion base (see emulsion base preparation described above) is added. When fully homogenized, ammonium hydroxide is added to the mixture.

For application to hair the peroxide base and the dye base are mixed together at a 1:1 ratio and applied to dry hair.

Examples 4-5

After Colorant Conditioners

| Ingredients | #5 Wt % | #6 Wt % | #7 Wt % |
|---|---|---|---|
| Deionized water | 61.95-qs | 60.95-qs | 61.95-qs |
| Emulsion base: | | | |
| Deionized water | 29.76 | 29.76 | 29.76 |
| Cetyl alcohol (1) | 2.25 | 2.25 | 2.25 |
| Stearyl alcohol (2) | 2.25 | 2.25 | 2.25 |
| Ceteareth-25 (3) | 1.50 | 1.50 | 1.50 |
| Phenoxyethanol (4) | 0.11 | 0.11 | 0.11 |
| Sodium benzoate (5) | 0.09 | 0.09 | 0.09 |
| Tetrasodium EDTA (87%) (6) | 0.04 | 0.04 | 0.04 |
| Citric acid anhydrous fine (14) | pH trim | pH trim | pH trim |
| Silicone premix: | | | |
| MQ resin sold under the name SR1000 by the company GE Bayer Silicones | 0.20 | 0.10 | 0.02 |
| Aminopolyether functional silicone fluid sold under the name XS69-B5476 by the company GE Bayer silicones | 1.80 | | |
| Aminofunctional polydimethylsiloxane sold under the name Dowcorning 2-8566 silicone fluids by the company Dow corning | | 1.98 | |
| Amino functional silicone fluid sold under the name Rhodorsil 21637 by the company Rhodia | | | 1.90 |

(14): available as citric acid anhydrous fine from Aldrich

Composition Preparation

The conditioner composition is prepared by adding to a vessel the deionized water and the emulsion base (see emulsion base preparation described above) while stirring. When homogenized citric acid is added to the mixture until the pH of the emulsion is between 5 and 6.

The functionalized silicones premix is prepared by premixing together the functionalised silicone fluid and the organosiloxane resin with agitation. The functionalised silicone premix is then added to the main mix and stirred until the desired particle size is obtained.

What is claimed is:

1. Fiber treatment composition comprising
   (1) a oil-in-water emulsion mixture having a $(\text{Tan}\delta)^{-1}$ of 0.001 to 0.1 consisting of
   (a) a functionalized silicone polymer selected from the group consisting of:

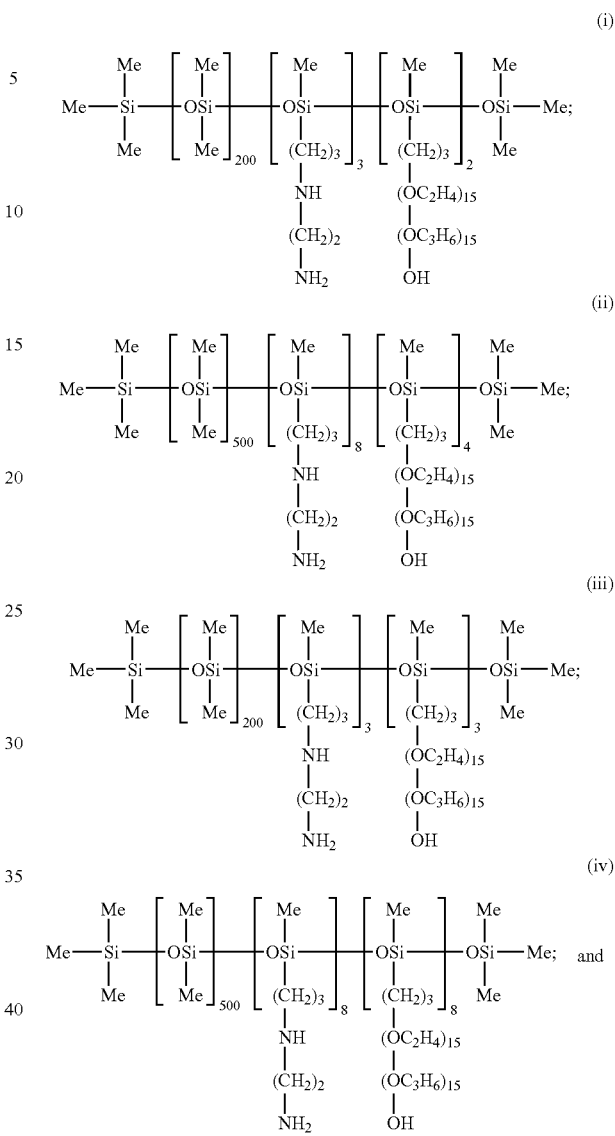

mixtures thereof;
   (b) a durability additive which is miscible with the functionalized silicone, said durability additive being an organosiloxane resin comprising repeating monofunctional $R_3SiO_{1/2}$ "M" units and quadrafunctional $SiO_2$ "Q" units, wherein said resin satisfies the relationship $R_nSiO_{(4-n)/2}$, wherein the value of n is about 1.2, wherein the ratio of said "M" to "Q" functional units is from about 0.7, and, wherein said resin is solid at about 25° C.;
   (c) an emulsifier; and
   (d) an aqueous continuous phase comprising water; and
   (2) a hair bleaching component, a hair dyeing component and combinations thereof.

2. Fiber treatment composition according to claim 1, wherein the interfacial tension of the functionalization silicone polymer is less than about 12 mN/m and the hydrophilicity index is less than or equal to about 99.5.

3. Fiber treatment composition according to claim 1, wherein the interfacial tension of the functionalization silicone polymer is less than about 8 mN/m and the hydrophilicity index is less than or equal to about 98.

4. Fiber treatment composition according to claim 1, wherein the ratio of functionalized silicone to durability additive is in the range from about 5:1 to about 1000:1.

5. Fiber treatment composition according to claim 1, wherein the composition comprising from about 0.1 to about 20wt. % of said of functionalized silicone polymer and durable additive mixture.

6. Fiber treatment composition according to claim 1, comprising 0.1% to about 15% based on the weight of the aqueous continuous phase of emulsifier.

7. Fiber treatment composition according to claim 1, comprising 0.1% to about 15% based on the weight of the aqueous continuous phase of emulsifier; wherein the emulsifier comprises one or more of an anionic surfactant, cationic surfactant, amphoteric surfactant, water-soluble polymeric surfactant, water soluble silicone-containing surfactant and a nonionic surfactant having an HLB greater than 10.

8. Fiber treatment composition according to claim 7, wherein the surfactant comprises $C_{16}$-$C_{22}$ fatty alcohols and/or fatty alcohol ethoxylates with about 1 to about 30 ethylene oxide groups.

9. Fiber treatment composition according to claim 8, wherein the surfactant comprises a mixture of $C_{16-22}$ fatty alcohols and $C_{16-22}$ fatty alcohol ethoxylates in a ratio of between about 10:1 to about 0.5:1.

10. Hair treatment kit comprising:
(a) an oxidative bleaching composition
(b) a dye composition; and
a fiber treatment composition according to claim 1 comprised within component
(a) and/or within component (b) and/or is provided as a separate component.

* * * * *